United States Patent [19]

Potts

[11] Patent Number: 5,299,582

[45] Date of Patent: Apr. 5, 1994

[54] SURGICAL ISOLATION APPARATUS

[75] Inventor: William E. Potts, Tallahassee, Fla.

[73] Assignee: Little Rapids Corporation, Green Bay, Wis.

[21] Appl. No.: 760,754

[22] Filed: Sep. 16, 1991

[51] Int. Cl.⁵ .......................................... A61B 19/12
[52] U.S. Cl. ...................................... 128/846; 128/849
[58] Field of Search ............... 128/846, 847, 849, 851, 128/852, 853, 854, 856; 604/317

[56] References Cited

U.S. PATENT DOCUMENTS

| 1,257,332 | 2/1918 | Erlandson | 128/847 X |
| 3,859,993 | 1/1975 | Bitner | 128/847 |
| 4,007,741 | 2/1977 | Waldrop et al. | 128/846 X |
| 4,223,669 | 9/1980 | Morledge | 128/849 X |
| 4,903,710 | 2/1990 | Jessamine et al. | 128/846 X |
| 4,930,169 | 6/1990 | Davison | 128/846 X |
| 4,998,538 | 3/1991 | Charowsky et al. | 128/856 |
| 5,111,850 | 5/1992 | Kunofsky | 128/846 X |

FOREIGN PATENT DOCUMENTS 8606272 11/1986 World Int. Prop. O. .......... 128/849

Primary Examiner—Robert A. Hafer
Assistant Examiner—Sam Rimell
Attorney, Agent, or Firm—Niro, Scavone, Haller & Niro

[57] ABSTRACT

A surgical isolation apparatus suitable for use in a variety of surgical procedures completely isolates operating personnel from the patent's blood, body fluids and contaminated irrigation fluids, while providing manual access to the operating area and permitting use of optical instruments such as endoscopes. The preferred embodiment of the invention is especially designed for transurethral prostatectomies, and can be fabricated simply and inexpensively from two sheets of transparent plastic.

45 Claims, 3 Drawing Sheets

SURGICAL ISOLATION APPARATUS

BACKGROUND OF THE INVENTION

I. Field of the Invention

Many surgical procedures expose operating personnel to the patient's blood and other body fluids, as well as to water and other liquids used for irrigation purposes during some surgical procedures. Such "operating fluids" may carry contagious diseases, such as the AIDS virus.

This invention relates to a disposable surgical isolation apparatus that completely protects operating personnel from contact with contaminated operating fluids, while providing full access to the patient for the hands of the operating personnel and for optical surgical instruments such as endoscopes. This invention eliminates the need for operating personnel to wear facemasks or cumbersome full-body protective clothing. Embodiments of the invention include provisions for sampling and collecting operating fluids during the surgical procedure; and for safe disposal the entire surgical isolation apparatus, together with any collected operating fluids, following the surgical procedure. The preferred embodiment is simply constructed of two sheets of transparent plastic, heat-sealed at the edges, to provide an economical device that can be disposed of after it has been contaminated.

II. Description of the Prior Art

The most popular current approach to management of operating fluids during operations like transurethral prostatectomies is simply to channel the fluids down the exterior of a surgical drape into a collection bag, which in turn may empty into a hose leading to a floor drain. The following U.S. Pat. Nos. describe variants on that approach: 4,414,968 (Amin); 4,462,396 (Wichman); 4,489,720 (Morris, et al.); 4,890,628 (Jackson); 4,378,794 (Collins); 4,471,769 (Lockhart); 4,570,628 (Neal); 4,596,245 (Morris), and 4,974,604 (Morris). Only in combination with full-body protective garments such as those disclosed in U.S. Pat. No. 4,535,481 (Ruth-Larson, et al.) and protective face shields like those disclosed in U.S. Pat. Nos. 4,834,068 (Gottesman) and 4,848,322 (Dash, et al.) can the foregoing arrangements provide any protection from contaminated operating fluids for the operating personnel. And even combined with such measures, protection is far from complete because operating fluids may still spatter or spill, contaminating the operating room environment.

U.S. Pat. No. 4,903,710 (Jessamine, et al.) discloses a drape of that attaches to the legs and feet of a patient in the lithotomy position, screening the patient's genital area from the physician and enclosing the working area at the back (i.e., facing away from the patient) and sides only (not at the front facing toward the patient, or at the top) by means of panels attached to the patient's lower legs (as shown in Jessamine's FIG. 5). Operating fluids that do not spatter or spill outside the partial enclosure formed by the drape can be channeled into a bucket (as shown in Jessamine's FIG. 3). There is no provision for collection of all operating fluids, and Jessamine's drape provides only partial protection for operating personnel standing in certain positions during the operation—for example, anyone standing near the patient's head would be unprotected. And, since Jessamine depends upon the patient's legs to support the drape, it is only usable for surgical procedures in which the patient is in the lithotomy position.

The purpose of the invention described in U.S. Pat. No. 4,926,882 (Lawrence) is to isolate the skull or ribcage of a cadaver from a person performing an autopsy, while providing an instrument port 24 to accommodate the shaft of an oscillating bone saw. When a craniotomy is to be performed, an adhesive strip 24 seals the bag around the shoulders of the cadaver; to remove the spinal chord a pair of adhesive strips are used, one around the neck 121 and the other just below the waist 122. Stiffening ribs 34, arranged in a cruciform pattern with its center at instrument port 24, spread the drape and hold it away from the working area while the sawing operation is being performed, but once the saw is withdrawn there is no provision for continued support of the drape. Nor is there need for such provision, since as Lawrence explains there is no flowing blood or other fluid in an autopsy, and the main reason any protection is needed is because the bone saw tends to disperse quiescent fluids into the air as an aerosol, a phenomenon that stops at the conclusion of the sawing operation. Thus, Lawrence does not provide any manual access through the shield to the working area. Lawrence also makes no provision for collecting operating fluids, and would be unusable for procedures requiring much irrigation even if it could be adapted for use on live patients.

U.S. Pat. No. 4,489,720 (Morris, et al.) discloses a drape intended for use during Cesarean deliveries. According to Morris, ordinary fluid management devices (in which the blood and other fluids run down the outside or upper surface of the drape and are channeled into a bag or receptacle attached to, or formed on the outer surface of the drape) are inappropriate for Cesarean deliveries because the patient lies too flat, or on one side, apparently providing insufficient slope to drain fluids into a bag attached outside the drape. Morris attempts to solve the problem by attaching the bag 19 to the inner surface of the drape, so it hangs down between the patient's legs. Fluids enter the bag through a fenestration 21 communicating between the upper surface of the drape and the bag 19. A flap 22, fitted with an adhesive strip 23, allows the bag to be sealed after the operation to prevent spilling of fluid as the sheet is removed. (Col. 3, line 64 through col. 4, line 5).

The resulting arrangement, however, is a complex multi-piece construction. And it is specifically adapted to a particular procedure: a Cesarean delivery. Most importantly, it does not provide any protection for the physician from contaminated blood and body fluids.

U.S. Pat. No. 4,471,769 (Lockhart) discloses a drape having one hammock-shaped member 8 that can be attached to the physician's chest by means of an adhesive strip 40, forming a concave surface with a drain hole 38 at its bottom. Again, however, contaminated operating fluids flow down an open trough directly in front of the physician's face, with no protection for the physician or other operating personnel.

There is a need for a surgical isolation apparatus that can accommodate a variety of surgical procedures, and that ensures complete isolation and containment of contaminated operating fluids while providing access to the operating area for the hands of the operating personnel, and for optical instruments such as endoscopes.

SUMMARY OF THE INVENTION

The apparatus of this invention provides a liquid-impermeable work enclosure that is attached at is bottom to the patient's skin around the operating area, and that supported above the operating area by attachment to the neck, shoulders, head or other part of the upper body of one of the operating personnel, or to an overhead support rod that may, for example, form part of a lighting fixture. Those support means do not depend upon positioning the patient in any particular position, such as the lithotomy position to which Jessamine's drape is adapted. Sealable apertures provide access for the hands of the operating personnel (which normally will be gloved), for the eyepiece of an optical instrument such as an endoscope and for wiring and plumbing. An attached filter and fluid collection pouch, optionally connected to a floor drain, allows management of operating fluids and maintains isolation of such fluids from operating personnel. In one embodiment of the invention, an integral disposal package can be sealed around the entire device, together with any collected operating fluids, at the conclusion of the operation to provide safe disposal.

Accordingly, one object of this invention is to provide a surgical isolation device that completely protects operating personnel from contact with contaminated operating fluids.

It is a further object of this invention to provide a surgical isolation device that can be used for a wide variety of surgical procedures, because it does not depend upon positioning the patient in one particular orientation such as the lithotomy position.

It is another object of this invention to provide a surgical isolation device that can be supported above the area of the patient upon which the operation is being performed either by attachment to the neck, shoulders, head or other part of the upper body of one of the operating personnel, or to an overhead support rod which may form part of a lighting fixture.

It is another object of this invention to provide a surgical isolation device usable with optical instruments such as endoscopes.

It is another object of this invention to provide a surgical isolation device that can accommodate the plumbing and electrical wiring needed for some surgical procedures.

It is still another object of this invention to provide a surgical isolation device that can provide a sample of operating fluids.

It is a further object of this invention to provide an integral disposal package for safe disposal of the surgical isolation device and any collected operating fluids.

DESCRIPTION OF THE EMBODIMENT OF FIG. 1

Figure 1:
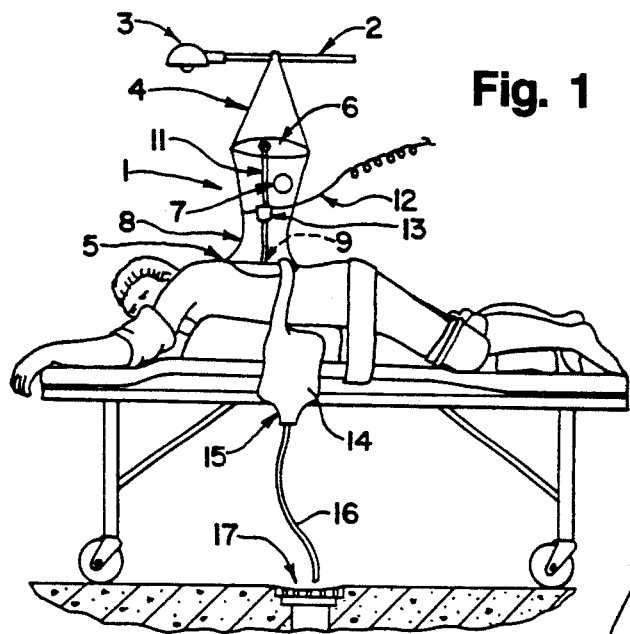
FIG. 1 shows an embodiment of the invention suitable for use in a variety of surgical procedures, positioned for an operation on the back of the patient.

FIG. 1 illustrates the surgical isolation device in position for a surgical procedure on the back of a patient, supported from an overhead support rod 2 which comprises any convenient part of a lighting fixture 3 by support means 4. The surgical isolation device comprises a roughly cylindrical, flexible plastic work enclosure 1, which is made of liquid-impermeable material such as transparent plastic. The bottom 5 of the work enclosure is attached to the skin of the patient surrounding the operating area by attachment means such as an adhesive coating faced with release paper, which paper is removed just before the isolation device is attached to the patient's skin. At least one sealable aperture 7 in the side 8 of the work enclosure provides access for the hands of the operating personnel to the interior working space 9 above the operating site. The top 6 of the work enclosure 1 comprises a shield of liquid-impermeable plastic, which may be transparent and which may be provided with a second sealable aperture 10 suitable for sealing around the eyepiece of an optical instrument 11, or around some other piece of surgical equipment such as a probe or catheter, if desired. Plumbing and wiring 12 enters the interior working space 9 through a third sealable aperture 13 in the side 8 of the work enclosure 1.

The apertures for hands, optical or surgical instrumentation and plumbing and wiring can be sealed with surgical tape. Other sealing methods known to those skilled in the art, such as elastic tie strips, also can be used.

A fluid collection pouch 14 communicates with the interior space 9 of the work enclosure 1, allowing operating fluids to drain by gravity away from the operating area into the fluid collection pouch during the operation. Filter means 15 at the bottom of fluid collection pouch 14 collects and retains any solid materials, and a tube 16 or similar means allows the liquid contents of the fluid collection pouch 14 to drain into a floor drain 17, if desired.

Figure 2:
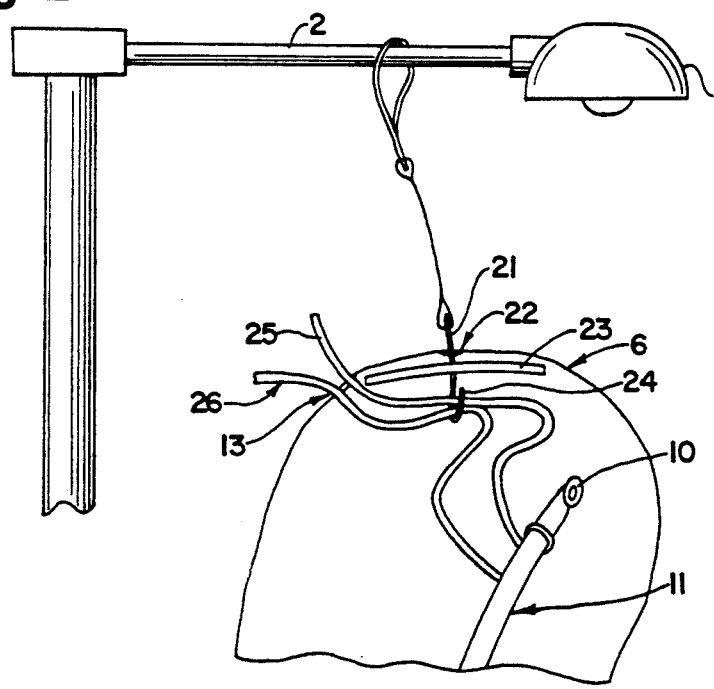
FIG. 2 shows a detail of one means for attaching the surgical isolation apparatus to an overhead support rod comprising part of a lighting fixture.

Referring now to FIG. 2, which shows the top 6 of the work enclosure 1, it can be seen that one means for supporting the top 6 is to suspend it from an overhead support rod 2 that forms part of a lighting fixture 3. A Velcro ® tape strip 18, which can encircle the overhead support rod 2, is attached to a peg or dowel 19 which can be press-fitted into one end of a piece of surgical tubing 20. One end of a hanger 21 is press-fitted into the other end of the surgical tubing 20. The hanger 21 protrudes through a small puncture 22 in the top 6 of the work enclosure 1. A spreading member 23 is affixed to hanger 21. The spreading member 23, which may be a plastic bar or a plastic cross, acts to support the top 6 of the work enclosure 1, cooperating with the sides 8 to define an interior working space 9. Thus, hanger 21 and spreading member 23, make it possible to fabricate work enclosure 1 out of a single piece of flexible plastic, obviating any need for top 6 to be rigid.

The bottom of hanger 21 terminates in a hook 24 which serves to support fiber optic line 25 and irrigation water line 26 within the interior working space 9, keeping those utility lines above and away from the area of the patient upon which the operation is to be performed.

Figure 3:
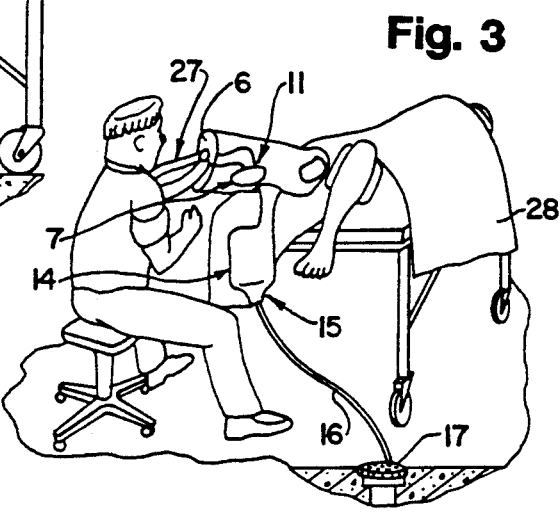
FIG. 3 shows another means for supporting the embodiment of FIG. 1, when that embodiment is utilized for genital surgery.

An alternate means for supporting the work enclosure 1 is to suspend its top transparent shield 6 from the shoulders, head or other part of the upper body of the physician by means of tie strip 27, as shown in FIG. 3. This support means is particularly suited to transurethral prostatectomies and related surgical and diagnostic procedures. The work enclosure 1 can be attached either directly to the patient's skin, as shown in FIG. 1, or to a conventional surgical drape 28 covering the rest of the patient's body, as shown in FIG. 3. In either instance, adhesive attachment means can be used.

DESCRIPTION OF THE EMBODIMENT OF FIG. 4

Figure 4:
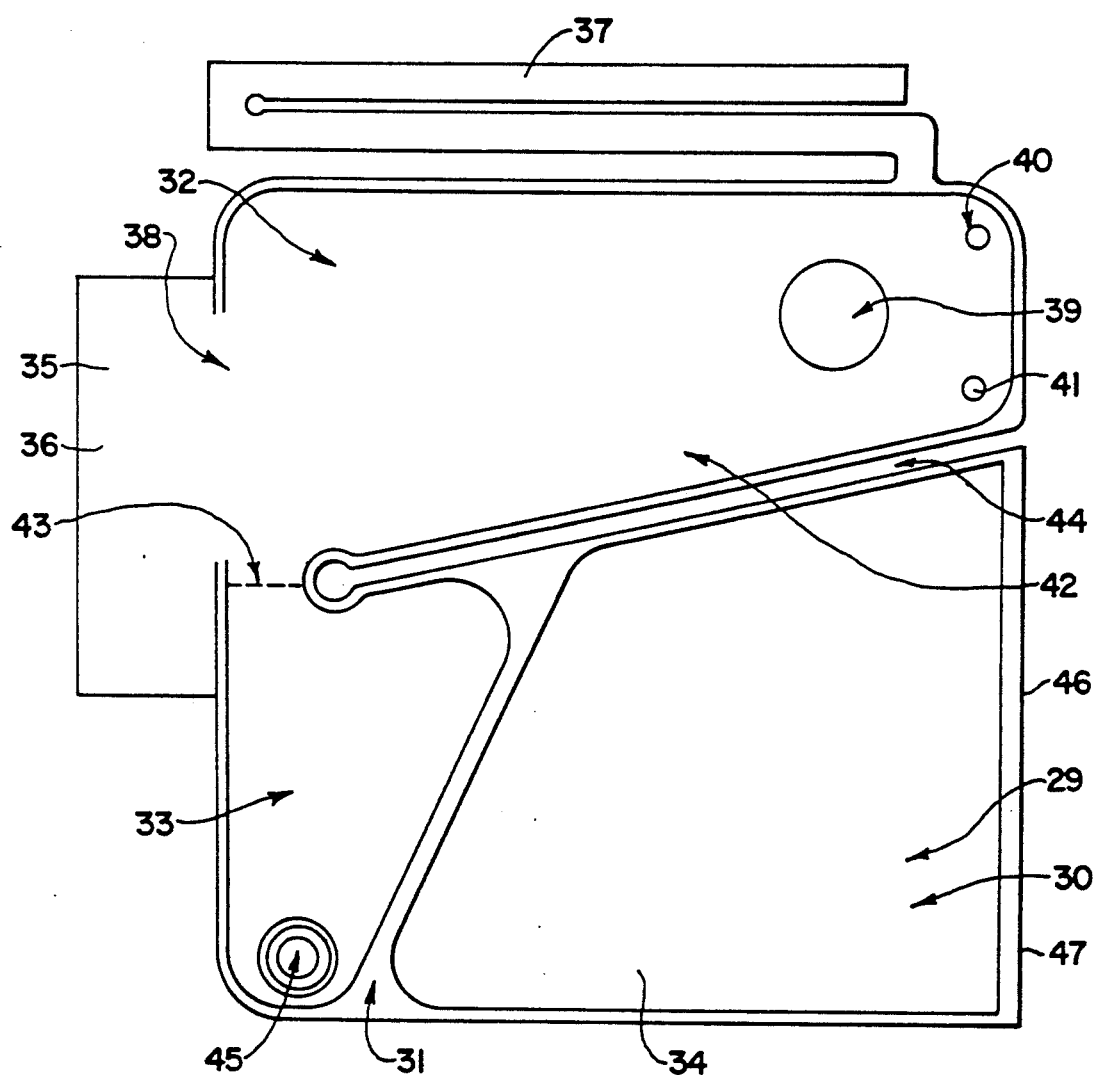
FIG. 4 illustrates another embodiment of the invention specifically designed for genital surgery. The embodiment of FIG. 4 includes an integral disposal package.

An alternate embodiment, particularly suited for genital surgery, is shown in FIG. 4. This embodiment is simple and inexpensive to fabricate, since it is made of two sheets of transparent plastic cut and heat-sealed to form the structure of the surgical isolation device.

The embodiment of FIG. 4 is constructed of two generally rectangular, flat sheets of transparent plastic 29 and 30, shown in plan view in FIG. 4. The two sheets are heat-sealed together along the heat seal line 31 shown in black on FIG. 4, thus subdividing the two sheets into a work enclosure 32, a fluid collection pouch 33 and an integral disposal package 34. In use, integral protruding tabs 35 and 36, which are faced with an adhesive coating and release paper (not shown), are attached to the patient's skin around the area of the patient upon which the surgical procedure is to be performed. Although a pair of integral protruding tabs is shown, it is possible to use one tab, or more than two, if desired. When the physician attaches tie strip 37 around his or her neck, shoulders, head or other part of his or her upper body, work enclosure 32 is expanded to form an interior working space 42 between the two sheets of plastic in the area of the work enclosure, within which the surgical procedure is performed. Alternatively, the work enclosure can be supported from an overhead support rod using the arrangement shown in FIG. 2.

Access to the working area of the patient is available at the bottom 38 of work enclosure 32, where the two sheets are not heat sealed together. When the patient is in the lithotomy position, for example in case of a transurethral prostatectomy, slot 44 (in which the material of the two sheets has been cut away completely) allows fluid collection pouch 33 and disposal package 34 to hang down between the patient's legs, leaving the operating area unobstructed.

Work enclosure 32 is provided with a plurality of first sealable apertures 39, permitting access for the hands of the operating personnel to the interior working space 42. At least one second sealable aperture 40 can accommodate the eyepiece of an optical instrument such as an endoscope, or any other desired piece of surgical equipment of appropriate function and size. And a third sealable aperture 41 can be used to admit plumbing and electrical wiring. As in the case of the embodiment of FIG. 1, the apertures for hands, optical instrumentation and plumbing and wiring can be sealed with surgical tape. Other sealing methods known to those skilled in the art, such as elastic tie strips, also can be used.

Fluid collection pouch 33 communicates with interior working space 42 through filter means 43, which in the embodiment shown in FIG. 4 comprises an area in which the two sheets 29 and 30 have been heat sealed together partially but not completely, allowing liquids to drain by gravity from interior working space 42 into fluid collection pouch 33 while retaining solids on filter means 43. Means for draining the liquid contents of the fluid collection pouch into a floor drain are provided, in the form of a fourth sealable aperture 45, which can be attached to a piece of tubing leading to the floor drain.

At the conclusion of the surgical procedure, the surgical isolation apparatus is detached from the patient's skin. Then, disposal package 34, which is open (i.e., not heat sealed) along its distal edge 46, can be everted to enclose the entire surgical isolation apparatus, including the work enclosure 32, the tie strip 37, the protruding tabs 35 and 36, and the fluid collection pouch 33, together with any collected operating fluid that has not been drained. Adhesive sealing means 47 (preferably comprising an adhesive coating on the exterior faces of both flexible sheets along edge 46, faced with release paper) can then be used to provide a liquid-impermeable seal around the entire apparatus, thus reducing the risk of contamination during disposal.

DESCRIPTION OF THE PREFERRED EMBODIMENT

Figure 5:
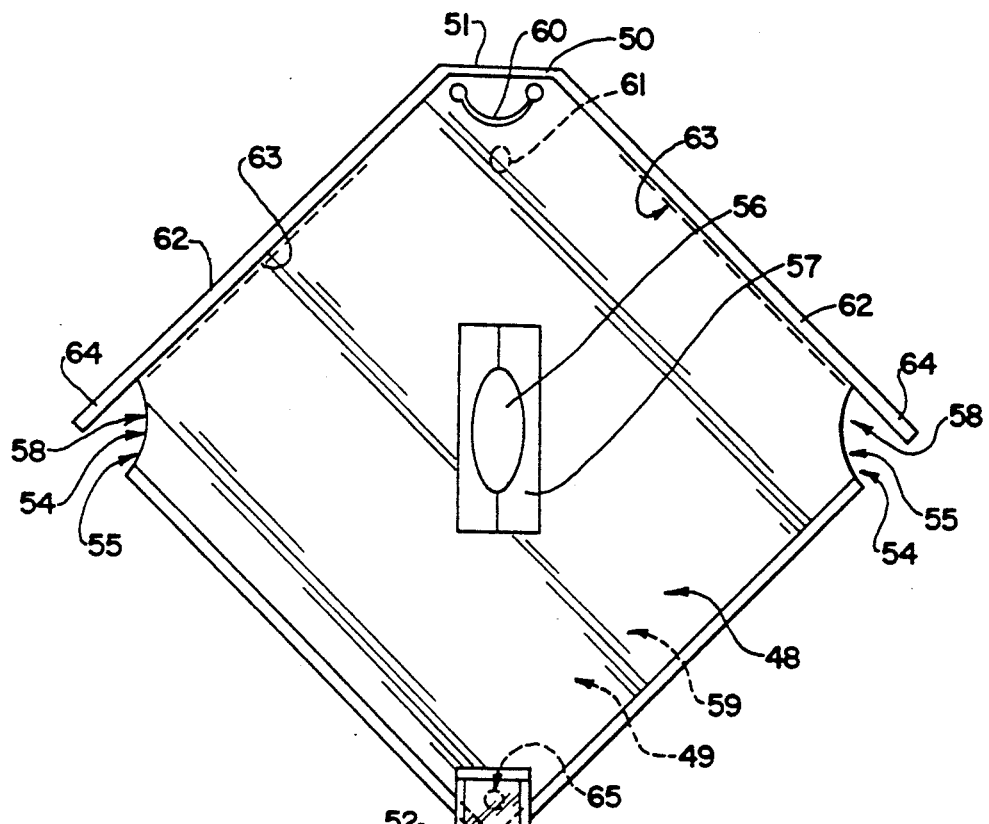
FIG. 5 shows the preferred embodiment of the invention, which is specifically designed for transurethral prostatectomies.
Figure 6:
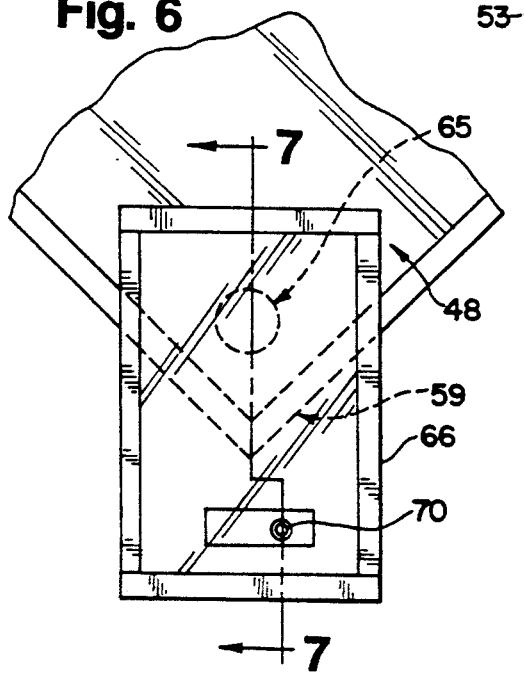
FIGS. 6 and 7 illustrate in greater detail the fluid collection pouch used in the preferred embodiment.
Figure 7:
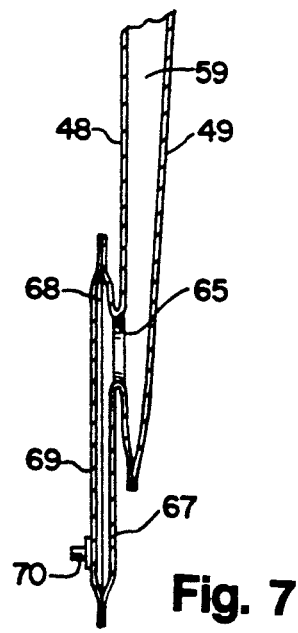

The preferred embodiment of the invention, shown in FIGS. 5–7, is designed specifically for transurethral prostatectomies. It comprises a first sheet of liquid-impermeable, transparent plastic 48, preferably between about 5 and about 10 mils in thickness, heat sealed around its perimeter to a second sheet of liquid impermeable, transparent plastic 49 having substantially the same shape as the first sheet but preferably having a thickness between about 1 mil and about 5 mils. It is most preferred that the first and second sheets be generally diamond-shaped; but elliptical and other suitable shapes, such as quadrilateral shapes, can be used as well.

Both sheets of plastic have coinciding top corners 50 and 51; bottom corners 52 and 53, and side corners 54 and 55. Roughly in the center of first sheet 48, first fenestration 56 in first sheet 48 provides access to the patient's scrotum and penis. First fenestration 56 is surrounded by adhesive attachment means 57, preferably comprising an adhesive coating on the exterior of first sheet 48 surrounding fenestration 56 and topped with release paper. At both side corners 54, 55 of sheets 48 and 49, first sealable apertures 58 furnish access to the interior working space 59 which is the interior volume defined by first sheet 48 and second sheet 49. At top corners 50 and 51 of first sheet 48 and second sheet 49, a third sealable aperture 60 is provided in both sheets, which allows access for plumbing and electrical wiring. An optional second sealable aperture 61 is provided in said second sheet 49, between said top corner 50 and the area of said second sheet 49 that overlies first fenestration 56. The optional, second aperture 61 can be sealed around the eyepiece of an optical instrument such as an endoscope, if desired, or around any other piece of surgical equipment or instrumentation of suitable function and size.

In use, the surgical isolation device is attached to the neck, shoulders, head or other part of the upper body of one of the operating personnel by means of tie straps 62, which are formed at the heat-sealed top edges of first and second sheets 48 and 49 by cutting lines of perforations 63 along the edges, allowing the distal ends 64 of tie strips 62 to be separated from the heat-sealed top edges of sheets 48 and 49 preparatory to attachment around the neck, shoulders, head or other part of the upper body of one of the operating personnel. Alternatively, the tie strips can be attached to an overhead support rod.

At the bottom corners 52 and 53 of first and second sheets 48 and 49, a second fenestration 65 in the first sheet 48 provides communication between the interior working space 59 and a fluid collection pouch 66. The preferred configuration of fluid collection pouch 66 is shown in FIGS. 6 and 7.

Referring now to FIGS. 6 and 7, it can be seen that fluid collection pouch 66 comprises an approximately rectangular bottom sheet 67 of liquid impermeable plastic, which is attached near the bottom corner 52 of first sheet 48 by heat sealing around the periphery of second fenestration 65. An intermediate sheet 68 of liquid-permeable plastic (which may be a perforated sheet of otherwise-impermeable plastic) and a top sheet 69 of liquid-impermeable plastic are heat sealed around their perimeters to bottom sheet 67, forming fluid collection pouch 66. Means for draining fluid collection pouch 66 is provided, in the form of plastic nozzle 70, which communicates through top sheet 69 with the interior of fluid collection pouch 66.

In use, operating fluid drains by gravity from interior working space 59 through second fenestration 65 into the interior of fluid collection pouch 66. When the means 70 for draining the pouch is in use, operating fluid will pass through intermediate sheet 68 and out drain means 70. Any solid material in the operating fluid will be retained by intermediate sheet 68.

It will be apparent to those of ordinary skill in the art that many changes and modifications could be made while remaining within the scope of the invention. For example, the plastic sheets 48 and 49 that define the interior working space of the preferred embodiment could be sealed together around their perimeters by adhesive rather than by heat sealing. It is my intention to cover all such equivalent structures, and to limit my invention only as specifically delineated in the following claims.

I claim:

1. A surgical isolation apparatus providing substantially complete isolation of all operating fluids from the operating personnel, comprising:
   a. a liquid-impermeable work enclosure having sides, a top and a bottom, defining an interior working space;
   b. means for attaching said bottom of said work enclosure to the patient surrounding the area of the patient upon which the operation is to be performed;
   c. means for supporting said top of said work enclosure above the area of the patient upon which the operation is to be performed;
   d. a plurality of first sealable apertures in said sides of said work enclosure permitting access to said interior working space for the hands of the operating personnel, and
   e. fully enclosed means for draining operating fluids from said bottom of said work enclosure.

2. The surgical isolation apparatus of claim 1, further comprising a transparent, liquid impermeable shield that forms said top of said work enclosure.

3. The surgical isolation apparatus of claim 1, further comprising at least on second aperture suitable for sealing around the lens portion of an optical surgical instrument.

4. The surgical isolation apparatus of claim 1, wherein said means for draining operating fluids further comprises a fluid collection pouch having a top portion in communication with said interior working space, and a bottom portion, whereby the operating fluids drain into said top portion of said fluid collection pouch.

5. The surgical isolation apparatus of claim 4, further comprising filter means in communication with said bottom portion of said fluid collection pouch for filtering the operating fluids and means for draining any collected operating fluids out of said fluid collection pouch and into a floor drain.

6. The surgical isolation apparatus of claim 1, wherein said means for attaching said bottom end of said work enclosure to the patient comprises an adhesive suitable for sealing said bottom of said work enclosure to the patient's skin, applied to said bottom of said work enclosure and faced with release paper.

7. The surgical isolation apparatus of claim 1, wherein said means for supporting said top of said working area further comprises means for attaching said top of said work enclosure to the upper body of one of the operating personnel.

8. The surgical isolation apparatus of claim I, wherein said means for supporting said top of said working area further comprises an overhead support rod, and means for attaching said top of said work enclosure to said overhead support rod.

9. The surgical isolation apparatus of claim 8, wherein said means for attaching said top of said work enclosure to said overhead support rod further comprises:
   a. a hanger that extends through said work enclosure opposite the area of the patient upon which the operation is to be performed;
   b. a spreading member attached to said hanger within said work enclosure, and
   c. means for suspending said hanger from said overhead support rod.

10. The surgical isolation apparatus of claim 1, further comprising at least one third sealable aperture permitting access to said interior working space for electrical wiring and tubing for carrying fluids.

11. A surgical isolation apparatus providing substantially complete isolation of all operating fluids from the operating personnel, comprising:
   a. a liquid-impermeable work enclosure having sides, a top and a bottom, defining an interior working space;
   b. attachment means for sealing said bottom of said work enclosure to the patient's skin surrounding the area of the patient upon which the operation is to be performed, said attachment means comprising an adhesive coating applied to said bottom of said work enclosure and faced with release paper;
   c. transparent shield forming said top of said work enclosure;
   d. means for attaching said transparent shield to the upper body of one of the operating personnel, whereby said transparent shield and said top of said work enclosure are supported above the area of the patient upon which the operation is to be performed;
   e. a plurality of first sealable apertures in said sides of said work enclosure permitting access to said interior working space for the hands of the operating personnel;

f. at least one second aperture suitable for sealing around the lens portion of an optical surgical instrument;

g. a fluid collection pouch in communication with said interior working space, whereby the operating fluids drain into said fluid collection pouch;

h. means for filtering the operating fluids and means for draining any collected operating fluids out of said fluid collection pouch and into a floor drain, and i. at least one third sealable aperture permitting access to said interior working space for electrical wiring and tubing for carrying fluids.

12. A surgical isolation apparatus providing substantially complete isolation of all operating fluids from the operating personnel, comprising:

a. two sheets of liquid-impermeable plastic material sealed together to subdivide the two sheets into a work enclosure, an interior working space defined by said work enclosure, a fluid collection pouch in communication with said interior working space, and an integral disposal package having an unsealed outer edge along which said two sheets of plastic are not heat-sealed together and that is not in communication with said interior working space and said fluid collection pouch; said disposal package being of sufficient size to contain said surgical isolation apparatus after use;

b. at least one integral protruding tab formed from the material of each of said sheets, suitable for attachment around the area of the patient's body upon which the surgical procedure is to be performed; and c. a plurality of first sealable apertures in said work enclosure and communicating with said interior working space, permitting access thereto for the hands of the operating personnel.

13. The surgical isolation apparatus of claim 12, wherein said sheets of liquid-impermeable plastic material are generally rectangular in shape and are sealed together by heat sealing.

14. The surgical isolation apparatus of claim 12, further comprising means for supporting said work enclosure above the area of the patient upon which the operation is to be performed.

15. The surgical isolation apparatus of claim 12, further comprising a pair of integral protruding tabs having adhesive coatings thereon, faced with release paper, suitable for attaching said pair of protruding tabs to the patient's skin.

16. The surgical isolation apparatus of claim 12, further comprising adhesive means situated along said unsealed outer edge of said disposal package for sealing said disposal package around said work enclosure and said fluid collection pouch at the conclusion of the surgical procedure.

17. The surgical isolation apparatus of claim 14, wherein said means for supporting said work enclosure comprises a tie strip attached to said work enclosure, suitable for attachment to the upper body of one of the operating personnel.

18. The surgical isolation apparatus of claim 14, wherein said means for supporting said work enclosure comprises an overhead support rod, and means for attaching said work enclosure to said overhead support rod.

19. The surgical isolation apparatus of claim 18, wherein said means for attaching said work enclosure to said overhead support rod further comprises:

a. a hanger that extends through said work enclosure opposite the area of the patient upon which the operation is to be performed;

b. a spreading member attached to said hanger within said work enclosure, and c. means for suspending said hanger from said overhead support rod.

20. The surgical isolation apparatus of claim 12, further comprising filter means located between said interior working space and said fluid collection pouch.

21. The surgical isolation apparatus of claim 20, wherein said filter means comprises an area in which said flat sheets have been partially heat sealed together.

22. The surgical isolation apparatus of claim 12, further comprising at least one second aperture in said work enclosure, communicating with said interior working space and suitable for sealing around the lens portion of an optical surgical instrument.

23. The surgical isolation apparatus of claim 12, further comprising at least one third sealable aperture in said work enclosure permitting access to said interior working space for electrical wiring and tubing for carrying fluids.

24. The surgical isolation apparatus of claim 12, further comprising means for draining any liquid contents of said fluid collection pouch into a floor drain.

25. A surgical isolation apparatus providing substantially complete isolation of all operating fluids from the operating personnel, comprising:

a. two generally rectangular, flat sheets of transparent, liquid-impermeable plastic material heat-sealed together to subdivide the two sheets into a work enclosure, a fluid collection pouch in communication with an interior working space defined by said work enclosure, and an integral disposal package having an unsealed outer edge along which said two sheets of plastic are not heat-sealed together and that is not in communication with said interior working space and said fluid collection pouch; said disposal package being of sufficient size to contain said surgical isolation apparatus after use;

b. adhesive means situated along said unsealed outer edge of said disposal package for sealing said disposal package around said work enclosure and said fluid collection pouch at the conclusion of the surgical procedure;

c. a filter located between said interior working space and said fluid collection pouch, said filter comprising an area in which said flat sheets have been partially heat sealed together;

d. means for draining any liquid contents of said fluid collection pouch into a floor drain;

e. a pair of integral protruding tabs formed from the material of said sheets, suitable for attachment around the area of the patient's body upon which the surgical procedure is to be performed;

f. adhesive coatings on said protruding tabs, faced with release paper, suitable for attaching said protruding tabs to the patient's skin;

g. a tie strip attached to said work enclosure suitable for attachment to the upper body of one of the operating personnel, whereby said work enclosure is supported above the area of the patient upon which the operation is to be performed;

h. a plurality of first sealable apertures in said work enclosure communicating with said interior working space and permitting access thereto for the hands of the operating personnel;
i. at least one second aperture in said work enclosure, communicating with said interior working space and suitable for sealing around the lens portion of an optical surgical instrument, and
j. at least one third sealable aperture in said work enclosure permitting access for said interior working space for electrical wiring and tubing for carrying fluids.

26. A surgical isolation apparatus providing substantially complete isolation of all operating fluids from the operating personnel, comprising:
   a. a first sheet of liquid impermeable plastic having an approximate center and a perimeter including corners;
   b. a first fenestration at said approximate center of said first sheet, of a size suitable for providing access to the area of a patient upon which the operation is to be performed;
   c. a second sheet of liquid impermeable plastic of substantially the same shape as said first sheet;
   d. a perimeter of said second sheet;
   e. sealed seams at the perimeters of said first and second sheets, joining said first and second sheets together to define an interior working space;
   f. first apertures in said first and second sheets permitting access to said interior working space for the hands of the operating personnel;
   g. means for supporting a portion of said first and second sheets above the area of the patient upon which the operation is to be performed;
   h. a fluid collection pouch attached to said bottom corner of said first sheet, in communication through a second fenestration in said bottom corner of said first sheet with said interior working space, whereby the operating fluids drain into said fluid collection pouch.

27. The surgical isolation apparatus of claim 26 in which said first sheet and said second sheet are generally diamond-shaped.

28. A surgical isolation apparatus providing substantially complete isolation of all operating fluids from the operating personnel, comprising:
   a. a first quadrilateral sheet of liquid impermeable plastic having an approximate center, four edges, a top corner, a bottom corner and two side corners;
   b. a perimeter of said first sheet defined by said four edges and said corners;
   c. a first fenestration at said approximate center of said first sheet, of a size suitable for providing access to the area of a patient upon which the operation is to be performed;
   d. a second sheet of liquid impermeable plastic of substantially the same shape as said first sheet, also having four edges, a top corner, a bottom corner and two side corners;
   e. a perimeter of said second sheet formed by said four sides and said corners;
   f. sealed seams at the perimeters of said first and said second sheets, joining said first and second sheets together to define an interior working space;
   g. first apertures in each of said side corners of said first and second sheets permitting access to said interior working space for the hands of the operating personnel;
   h. means for supporting said top corners of said first and second sheets above the area of the patient upon which the operation is to be performed;
   i. a fluid collection pouch attached to said bottom corner of said first sheet, in communication through a second fenestration in said bottom corner of said first sheet with said interior working space, whereby the operating fluids drain into said fluid collection pouch.

29. The surgical isolation apparatus of claim 28 in which said quadrilateral first and second sheets are of a substantially diamond shape.

30. The surgical isolation apparatus of claim 28, further comprising a fluid collection pouch attached to said bottom corner of said first sheet, in communication through a second fenestration in said bottom corner of said first sheet with said interior working space, whereby the operating fluids drain into said fluid collection pouch.

31. The surgical isolation apparatus of claim 30, further comprising filter means intermediate said interior working space and said fluid collection pouch.

32. The surgical isolation apparatus of claim 31, further comprising means for draining the liquid contents of said fluid collection pouch into a floor drain.

33. The surgical isolation apparatus of claim 30, wherein said fluid collection pouch further comprises:
   a. a bottom sheet of liquid impermeable plastic attached to said bottom corner of said first sheet around the periphery of a second fenestration in said bottom corner of said first sheet;
   b. an intermediate filter sheet of perforated, liquid permeable plastic having substantially the same shape as said bottom sheet and heat sealed around its perimeter to the perimeter of said bottom sheet;
   c. a top sheet of liquid impermeable plastic having substantially the same shape as said bottom sheet and heat sealed around its perimeter to the perimeters of said bottom sheet and said intermediate filter sheet, and
   d. means situated in said top sheet for draining the liquid contents of said fluid collection pouch into a floor drain, after the liquid contents have passed through said intermediate filter sheet.

34. The surgical isolation apparatus of claim 28, further comprising means for sealing the edges of said first apertures around the forearms of the operating personnel.

35. The surgical isolation apparatus of claim 28, further comprising adhesive sealing means surrounding said first fenestration for sealing said first sheet to the patient's skin surrounding the area of the patient upon which the operation is to be performed.

36. The surgical isolation apparatus of claim 28, wherein said means for supporting said top corners of said first and second sheets further comprises means for attaching said top corners of said sheets to the upper body of one of the operating personnel.

37. The surgical isolation apparatus of claim 36, wherein said means for attaching said top corners of said first and second sheets to the upper body of one of the operating personnel further comprises tie strips of plastic integrally formed along the top two of said edges of said first and second sheets and separated therefrom by lines of perforations extending parallel to said top two edges and toward said top corner.

38. The surgical isolation apparatus of claim 28, wherein said means for supporting said top corners of said first and second sheets further comprises an overhead support rod, to which said tie strips are attached.

39. The surgical isolation apparatus of claim 28, further comprising at least one second aperture in said second sheet suitable for sealing around the lens portion of an optical surgical instrument.

40. The surgical isolation apparatus of claim 28, further comprising at least one third sealable aperture at said top corners of said first and second sheets, permitting access to said interior working space for electrical wiring and tubing for carrying fluids.

41. The surgical isolation apparatus of claim 28, wherein said first sheet is made of transparent plastic having a thickness between about 5 mils and about 10 mils.

42. The surgical isolation apparatus of claim 28, wherein said second sheet is made of transparent plastic having a thickness between about 1 mil and about 5 mils.

43. A surgical isolation apparatus providing substantially complete isolation of all operating fluids from the operating personnel, comprising:
 a. a first generally diamond-shaped sheet of liquid impermeable material having four edges, a top corner, a bottom corner and two side corners;
 b. a first fenestration at the approximate center of said first sheet, of a size suitable for providing access to the genital organs of a patient;
 c. adhesive sealing means surrounding said first fenestration for sealing said first sheet to the patient's skin;
 d. a second sheet of liquid impermeable material of substantially the same shape as said first sheet, also having four edges, a top corner, a bottom corner and two side corners, and joined by sealed seams at its edges to said edges of said first sheet, defining an interior working space;
 e. first apertures in each of said side corners of said first and second sheets permitting access to said interior working space for the hands of the operating personnel;
 f. means for attaching said top corners of said sheets to the upper body of one of the operating personnel, whereby said top corners of said first and second sheets are supported above the area of the patient upon which the operation is to be performed;
 g. means for sealing the edges of said first apertures around the forearms of the operating personnel;
 h. at least one second aperture in said second sheet suitable for sealing around the lens portion of an optical surgical instrument, and
 i. at least one third aperture at said top corners of said first and second sheets, permitting access to said interior working space for electrical wiring and tubing for carrying fluids.

44. The surgical isolation apparatus of claim 43, further comprising:
 a. a fluid collection pouch attached to said bottom corner of said first sheet, in communication through a second fenestration in said bottom corner of said first sheet with said interior working space, whereby the operating fluids drain into said fluid collection pouch;
 b. filter means intermediate said interior working space and said fluid collection pouch, and
 c. means for draining the liquid contents of said fluid collection pouch into a floor drain.

45. The surgical isolation apparatus of claim 42, further comprising a fluid collection pouch comprising:
 a. a bottom sheet of liquid impermeable plastic attached to said bottom corner of said first sheet around the periphery of a second fenestration in said bottom corner of said first sheet;
 b. an intermediate filter sheet of perforated, liquid permeable plastic having substantially the same shape as said bottom sheet and heat sealed around its perimeter to the perimeter of said bottom sheet;
 c. a top sheet of liquid impermeable plastic having substantially the same shape as said bottom sheet and heat sealed around its perimeter to the perimeters of said bottom sheet and said intermediate filter sheet;
 d. means situated in said top sheet for draining the liquid contents of said fluid collection pouch into a floor drain, after the liquid contents have passed through said intermediate filter sheet.

* * * * *